United States Patent [19]

Purgason

[11] 3,991,115

[45] Nov. 9, 1976

[54] PROCESS FOR THE PREPARATION OF CYCLOHEXANONE OXIME

[75] Inventor: Richard Lynn Purgason, Richmond, Va.

[73] Assignee: Allied Chemical Corporation, Morris Township, N.J.

[22] Filed: Nov. 19, 1975

[21] Appl. No.: 633,208

[52] U.S. Cl. .............................. 260/566 A; 423/387
[51] Int. Cl.$^2$ ....................................... C07C 131/04
[58] Field of Search ................. 260/566 A; 423/387

[56] References Cited
UNITED STATES PATENTS 3,070,627  12/1962  Bostian et al. .................. 260/566 A
3,948,988  4/1976   de Rooij ......................... 260/566 A

FOREIGN PATENTS OR APPLICATIONS 651,447  10/1962  Canada ........................ 260/566 A Primary Examiner—Gerald A. Schwartz
Attorney, Agent, or Firm—Fred L. Kelly

[57] ABSTRACT

This invention relates to a process for the production of cyclohexanone oxime by reacting cyclohexanone with excess aqueous hydroxylamine in the presence of excess ammonia. More specifically, the invention relates to improving yields of the oxime while reducing undesirable by-product formation by use of two or more stages of reaction with correlated adjustment of reaction conditions in each stage. The invention also involves improved recovery of the unreacted hydroxylamine reactant for recycle in the process.

10 Claims, No Drawings

PROCESS FOR THE PREPARATION OF CYCLOHEXANONE OXIME

BACKGROUND OF THE INVENTION

This invention relates to the synthesis of cyclohexanone oxime by reacting cyclohexanone with hydroxylamine. Cyclohexanone oxime, as is well known, is an intermediate useful in the production of caprolactam by the Beckmann rearrangement. One of the more important uses of caprolactam is in the production of nylon type fibers.

The synthesis of cyclohexanone oxime by reacting cyclohexanone with an excess of hydroxylamine over the theoretical amount for formation of cyclohexanone oxime has been suggested. The excess of hydroxylamine assures complete utilization of the cyclohexanone which otherwise tends to contaminate the oxime product. Hydroxylamine sulfate solution produced by the hydrolysis of hydroxylamine disulfonate has been suggested as the source of hydroxylamine employed in such synthesis.

Canadian Pat. No. 651,447, granted Oct. 30, 1962, disclosed a process for recovering hydroxylamine values from aqueous ammonium sulfate brine by extracting the brine at a pH of about 2.5 or higher with cyclohexanone in a mol ratio of at least about 5 to 1, preferably between 7 and 1 and about 10 to 1, at a temperature of from 40° to 70° C. and recovering an organic distillate consisting essentially of cyclohexanone from the brine raffinate by steam distilling off at least about 1%, but not more than about 4%, by weight of the raffinate. By hydroxylamine values is meant hydroxylamine sulfonate or other forms of hydrolyzable hydroxylamine derivatives present in the aqueous ammonium sulfate brine.

The oximation, as described, including the use of hydroxylamine sulfate liquor produced by boiling the disulfonate for about one-half hour as the source of the hydroxylamine, invariably results in some lactam formation during the oximation and also in the formation of tars which contaminate the oxime product. While the reason for tar formation is not fully known, it is believed in part at least to be due to reaction between lactam and hydroxylamine monosulfonate extracted from the ammonium sulfate brine and recycled through the oximation reaction zone. Thus the process as proposed not only results in a loss of reactants due to the formation of lactam, but also results in an oxime product contaminated with undesirable tars.

More recently, U.S. Pat. No. 3,070,627, granted Dec. 25, 1962, disclosed a process of synthesizing cyclohexanone oxime in which during the oximation of the cyclohexanone, the formation of lactam is minimized and in which, notwithstanding the recycling through the oximation reaction zone of the cyclohexanone extractant employed to recovery hydroxylamine values including the cyclohexanone oxime content of the aqueous ammonium sulfate brine, the formation of tars which tend to contaminate the oxime product is also minimized if not completely prevented.

In accordance with this patent, hydroxylamine disulfonate produced as is well known by the reaction of ammonium nitrate, sulfur dioxide and ammonia is hydrolyzed to convert at least 97% of the ammonium hydroxylamine monosulfonate produced when the disulfonate is completely hydrolyzed to a hydroxylamine reactant containing hydroxylamine sulfate, and/or hydroxylamine acid sulfate, ammonium sulfate and/or ammonium bisulfate. The resultant hydroxylamine reactant is introduced into the oximation zone; into this zone is also fed (a) the cyclohexanone extract from the extraction of the ammonium sulfate brine, which cyclohexanone extract contains hydroxylamine values removed from the brine, (b) the organic distillate consisting essentially of cyclohexanone removed from the brine raffinate, and (c) additional cyclohexanone if needed, to thus provide in the oximator a reaction mixture containing at least 5, preferably from about 5 to 15, mol percent of hydroxylamine over and above the theoretical amount required for reaction with the cyclohexanone. Ammonia is introduced into the reaction mixture while agitating to produce at the completion of the oximation a reaction mixture having a pH of from 3 to 3.5, preferably 3.2 to precipitate the cyclohexanone oxime. The precipitate is separated from the ammonium sulfate mother liquor or brine by a centrifugal separator or by filtration.

Although the process of U.S. Pat. No. 3,070,627 is considered a major contribution to this art, research efforts have been continued in an effort to improve the process.

The present invention is an improvement offering advantages of very high yields and/or low production of by-products and/or improved recovery of the hydroxylamine used in excess in the oximation step of the process. This improvement consists in a combination of steps and conditions to be employed as described hereinafter.

SUMMARY OF THE INVENTION

The present invention may be summarized as follows.

A continuous process for producing cyclohexanone oxime from cyclohexanone in two or more reaction zones, by action thereon of hydroxylamine in the form of a hydroxylamine reactant prepared by mixing ammonium hydroxylamine disulfonate with water and heating the resultant mixture to a temperature of at least 105° C. until at least 99.5% of the ammonium hydroxylamine monosulfonate produced in the hydrolysis is hydrolyzed, which process comprises:

a. feeding substantially all of the hydroxylamine reactant to only the first reaction zone;

b. adding cyclohexanone to the reaction mixture in the first reaction zone, said cyclohexanone being in the form of cyclohexanone extract containing hydroxylamine values recovered in step (k) of the process, said cyclohexanone being added to said first reaction zone with vigorous agitation of sufficient intensity to destroy localized concentrations of cyclohexanone in the reaction mixture;

c. adding ammonia to the reaction mixture in the first reaction zone until the reaction mixture has a pH within the range of from 6.5 to 8.0;

d. circulating the reaction mixture in the first reaction zone at a rate at least 20 times the rate of feed of cyclohexanone to said zone;

e. carrying out the reaction in the first reaction zone at a temperature of from 70° to 95° C., and establishing a circulating reaction mixture in the first reaction zone having a pH of 6.5 to 8.0 and a mol ratio of hydroxylamine:cyclohexanone of from 1.05:1 to 1.15:1;

f. adding to the second and each subsequent zone, if any, a portion of the reaction mixture from the preceding zone;

g. carrying out the reaction in the second and each subsequent reaction zone, if any, at a temperature of from 70° to 95° C. with agitation until conversion of the cyclohexanone to cyclohexanone oxime is substantially complete;

h. withdrawing a stream comprising molten cyclohexanone oxime and ammonium sulfate brine from the last reaction zone;

i. separating the molten cyclohexanone oxime from the ammonium sulfate brine;

j. adjusting the pH of the ammonium sulfate brine to 7.0 to 9.0 by addition of an alkaline material selected from the group consisting of alkali metal hydroxides, alkali metal carbonates, and ammonia;

k. extracting the ammonium sulfate brine with cyclohexanone employing substantially all of cyclohexanone fed to the process, said extraction being carried out at a temperature of 70° to 95° C., whereby substantially all of the hydrolyzed hydroxylamine monosulfonate is extracted from the brine and reacted with the cyclohexanone; and l. introducing the cyclohexanone extract into step (b).

DESCRIPTION OF THE PREFERRED EMBODIMENT

The preferred process of the present invention is summarized as follows:

A continuous process for producing cyclohexanone oxime from cyclohexanone in two or more reaction zones, by action thereon of hydroxylamine in the form of a hydroxylamine reactant prepared by mixing ammonium hydroxylamine disulfonate with water and heating the resultant mixture to a temperature of 125° to 160° C. until at least 99.8% of the ammonium hydroxylamine monosulfonate produced in the hydrolysis is hydrolyzed, which process comprises:

a. feeding substantially all of the hydroxylamine reactant to only the first reaction zone;

b. adding cyclohexanone to the reaction mixture in the first reaction zone, said cyclohexanone being in the form of cyclohexanone extract containing hydroxylamine values recovered in step (k) of the process, said cyclohexanone being added to said first reaction zone with vigorous agitation of sufficient intensity to destroy localized concentrations of cyclohexanone in the reaction mixture;

c. adding ammonia to the reaction mixture in the first reaction zone until the reaction mixture has a pH within the range of from 7.0 to 7.5;

d. circulating the reaction mixture in the first reaction zone at a rate of 20 to 60 times the rate of feed of cyclohexanone to said zone;

e. carrying out the reaction in the first reaction zone at a temperature of from 75° to 85° C., and establishing a circulating reaction mixture in the first reaction zone having a pH of 7.0 to 7.5 and a mol ratio of hydroxylamine:cyclohexanone of from 1.05:1 to 1.15:1;

f. adding to the second and each subsequent zone, if any, a portion of the reaction mixture from the preceding zone;

g. carrying out the reaction in the second and each subsequent reaction zone, if any, at a temperature of from 75° to 85° C. with agitation until conversion of the cyclohexanone to cyclohexanone oxime is substantially complete;

h. withdrawing a stream comprising molten cyclohexanone oxime and ammonium sulfate brine from the last reaction zone;

i. separating the molten cyclohexanone oxime from the ammonium sulfate brine;

j. adjusting the pH of the ammonium sulfate brine to 7.5 to 9.0 by addition of ammonia;

k. extracting the ammonium sulfate brine with cyclohexanone employing substantially all of cyclohexanone fed to the process, said extraction being carried out at a temperature of 75° to 85° C., whereby substantially all of the hydrolyzed hydroxylamine monosulfonate is extracted and reacted with the cyclohexanone; and l. introducing the cyclohexanone extract into step (b).

The residence time of the cyclohexanone in contact with hydroxylamine reactant in the first reaction zone may be as short as a few minutes. An interesting finding in the production of cyclohexanone oxime in accordance with the present process is that the oxime formation is predominantly mass transfer controlled. With adequate agitation, reaction rates are as much as 2,000 fold those quoted in the literature. Accordingly, in the first oximation reaction zone, the reaction is desirably conducted in a circulating reaction loop composed of a very large pump, a heat exchanger and a small tank for product draw-off. In this system, the cyclohexanone is introduced along with a 5–15% molar excess of the hydroxylamine reactant. The pH is controlled within the preferred range of from 7.0 to 7.5 by automatic addition of ammonia to the circulating reaction mixture. The temperature of the reaction mixture is maintained at 75°–85° C. to prevent solidification of the oxime. The data indicate that the optimum rate of circulating the reaction mixture in said first reaction zone is 20 to 60 times the rate of feed of cyclohexanone to said zone. Circulation rate may be maintained using a conventional pump or a conventional in-line mixer (i.e., a high speed turbine impeller or like mixer or blender located in the circulation line). By use of the above preferred features of this process, the oximation reaction is normally at least 99 percent complete in the first reaction zone. The additional reaction zone or zones permit substantial completion of the reaction within a total reaction time of about 14 to 28 minutes.

A two-phase mixture of cyclohexanone oxime and ammonium sulfate brine is withdrawn from the last reaction zone and fed to a decanter where the cyclohexanone oxime floats free. Product oxime is separated containing approximately 5 percent water and less than 50 ppm ammonium sulfate. This oxime product is suitable for the production of caprolactam by known procedures.

The ammonium sulfate brine containing the excess hydroxylamine reactant from the oximation reaction is withdrawn from the decanter, and sufficient ammonia is added to adjust the pH to 7.5 to 9.0. This brine is then extracted with cyclohexanone employing substantially all of the cyclohexanone fed to the overall process. The brine is desirably extracted by adding the brine and cyclohexanone to the suction side of a pump used to transfer the mixture to a second decanter. The mixing achieved by this pump quantitatively converts the hydrolyzed hydroxylamine monosulfonate to cyclohexanone oxime, which dissolves in the excess cyclohexanone. Any unhydrolyzed hydroxylamine monosulfonate which may be present does not react but remains in the ammonium sulfate brine. This mixture is then separated in a second decanter, the upper organic layer serving as feed for the oximation step. The lower ammonium sulfate layer contains about 0.1% cyclohexanone which is recovered by steam stripping. After the stripping, the residual ammonium sulfate solution is sent to a recovery area where the water is evaporated and the ammonium sulfate converted to a crystalline solid.

The following examples are specific embodiments of this process, illustrating this invention. (Parts and percentages are by weight unless otherwise indicated).

EXAMPLE 1

The hydroxylamine reactant was prepared by continuously feeding 3,240 parts per hour of a solution containing about 31 percent ammonium hydroxylamine disulfonate and about 64 percent water to a hydrolysis system composed of two titanium reactors operating in series arrangement at a temperature of 145° C. and a pressure of 45 p.s.i.g. Average retention time was about 1 hour and 99.8% hydrolysis took place.

About 737 parts per hour of the hydroxylamine reactant solution thus produced and 100 parts per hour of a recycle stream containing 89 percent cyclohexanone and 11 percent cyclohexanone oxime were continuously fed to a first reaction zone containing a circulating reaction mixture having a mol ratio of hydroxylamine:cyclohexanone of about 1.1:1 and a pH of about 7.0. Equipment consisted of a circulation pump connected in series with a heat exchanger and a tank for product draw-off, said equipment being arranged for circulating the reaction mixture at a rate 40 times the rate of feed of cyclohexanone. All equipment and piping in contact with the reaction mixture was 316 stainless steel. The pH of the reaction mixture was controlled at about 7.0 by addition of about 38 parts per hour of ammonia. The temperature of the circulating reaction mixture exit the heat exchanger was maintained at 80° C. and the peak temperature in the reaction mixture was about 85° C. The hydroxylamine:cyclohexanone mol ratio of about 1.1:1 in the circulating reaction mixture was maintained by adjusting the feed of hydroxylamine reactant. Average retention time in the first reaction zone was about 7 minutes and the oximation reaction was 99.6 percent complete in said first reaction zone.

From the first reaction zone, a portion of the reaction mass equivalent to the feed thereto was continuously removed and fed to three agitated vessels connected in cascade and held at about 75°–80° C., to provide additional reaction time. Retention time in each vessel was about 7 minutes. Here the already small concentration of cyclohexanone from the first reaction zone was halved to about 0.2 percent of cyclohexanone fed to the first reaction zone.

Exit the reaction system, a two-phase mixture of molten cyclohexanone oxime and ammonium sulfate brine was sent to a decanter where the cyclohexanone oxime floated free. The cyclohexanone oxime was decanted containing approximately 5 percent water and less than 50 ppm ammonium sulfate.

The ammonium sulfate brine containing about 39 percent ammonium sulfate, about 0.04 percent unhydrolyzed hydroxylamine monosulfonate, and about 2 percent hydrolyzed hydroxylamine monosulfonate was withdrawn from the decanter and sufficient ammonia was added to the brine to adjust the pH to about 7.7.

This alkaline ammonium sulfate brine was then extracted to recover hydroxylamine values by reaction with excess cyclohexanone employing substantially all of the cyclohexanone fed to the overall process. The extraction was carried out by adding the ammonium sulfate solution and cyclohexanone to the suction side of a pump which was also used to transfer the mixture to a second decanter. About 12 parts of cyclohexanone was added for each 100 parts of ammonium sulfate brine fed to the pump. The mixing achieved by the pump converted substantially all of the hydrolyzed hydroxylamine monosulfonate to cyclohexanone oxime, and the resulting oxime dissolved in the excess cyclohexanone. During extraction, the pH of the reaction mass decreased to about 4.3 and the hydroxylamine content of the ammonium sulfate solution was reduced to about 0.04 percent, substantially all of said hydroxylamine being in the form of unhydrolyzed hydroxylamine monosulfonate. The mixture was then separated in the second decanter, the upper organic layer serving as feed to the first oximation zone. The lower ammonium sulfate layer was containing about 40 percent ammonium sulfate and about 0.1 percent cyclohexanone was fed to a packed stripping tower where the cyclohexanone was recovered by steam stripping. After stripping, the residual ammonium sulfate solution, essentially free from organic materials was sent to an ammonium sulfate recover unit where the water was evaporated and the ammonium sulfate converted to a crystalline solid.

EXAMPLE 2

The procedure of Example 1 was followed except that a conventional agitated reactor was used in the first reaction zone instead of the pumped, rapidly circulating reaction mass of Example 1. It was found that about 3.5 hours of retention time was required to obtain yields of oxime comparable to those of Example 1. Accordingly, the oximation reaction system is an important feature of the present process. It is also important that by use of the present reaction system, the addition of reactants can be easily controlled and the temperature of the reaction can be maintained at optimum conditions by pumping the rapidly circulating reaction mixture through a heat exchanger.

EXAMPLE 3

The procedure of Example 1 was followed except that the reaction mass in the first reaction zone was circulated at a rate 60 times the feed of cyclohexanone to said zone. Results indicated that the increased circulation rate gave no significant improvement in reaction time or yield over results obtained in Example 1. However, a circulation rate at least 20 times the feed of the cyclohexanone is desirable for adequate cooling of the reaction mixture in the heat exchanger.

EXAMPLE 4.

The procedure of Example 1 was followed except that the ammonium sulfate brine recovered from the first decanter was treated with sufficient ammonia to adjust the pH of the solution within the range 5.9 to 9.0. Solutions having different pH values were then extracted with cyclohexanone to extract hydroxylamine values as described in Example 1, and the percent hydroxylamine in the solution after extraction was determined. The following table demonstrates the criticalness of pH on the recovery of the hydroxylamine values from the ammonium sulfate solution.

TABLE I

| Adjusted pH of ammonium sulfate solution | Percent hydroxylamine in ammonium sulfate solution after extraction |
|---|---|
| 5.9 | 0.225 |
| 7.0 | 0.060 |
| 7.5 | 0.040 |
| 8.0 | 0.040 |
| 8.5 | 0.040 |
| 9.0 | 0.030 |

These data indicate that it is desirable to adjust the pH of the ammonium sulfate solution within the range 7.0 to 9.0. Preferably, the pH of the ammonium sulfate solution is adjusted to 7.5 to 9.0.

I claim:
1. A continuous process for producing cyclohexanone oxime from cyclohexanone in two or more reaction zones, by action thereon of hydroxylamine in the form of a hydroxylamine reactant prepared by mixing ammonium hydroxylamine disulfonate with water and heating the resultant mixture to a temperature of at least 105° C. until at least 99.5% of the ammonium hydroxylamine monosulfonate produced in the hydrolysis is hydrolyzed, which process comprises:
   a. feeding substantially all of the hydroxylamine reactant to only the first reaction zone;
   b. adding cyclohexanone to the reaction mixture in the first reaction zone, said cyclohexanone being in the form of cyclohexanone extract containing hydroxylamine values recovered in step (k) of the process, said cyclohexanone being added to said first reaction zone with vigorous agitation of sufficient intensity to destroy localized concentrations of cyclohexanone in the reaction mixture;
   c. adding ammonia to the reaction mixture in the first reaction zone until the reaction mixture has a pH within the range of from 6.5 to 8.0;
   d. circulating the reaction mixture in the first reaction zone at a rate at least 20 times the rate of feed of cyclohexanone to said zone;
   e. carrying out the reaction in the first reaction zone at a temperature of from 70° to 95° C., and establishing a circulating reaction mixture in the first reaction zone having a pH of 6.5 to 8.0 and a mol ratio of hydroxylamine:cyclohexanone of from 1.05:1 to 1.15:1;
   f. adding to the second and each subsequent zone, if any, a portion of the reaction mixture from the preceding zone;
   g. carrying out the reaction in the second and each subsequent reaction zone, if any, at a temperature of from 70° to 95° C. with agitation until conversion of the cyclohexanone to cyclohexanone oxime is substantially complete;
   h. withdrawing a stream comprising molten cyclohexanone oxime and ammonium sulfate brine from the last reaction zone;
   i. separating the molten cyclohexanone oxime from the ammonium sulfate brine;
   j. adjusting the pH of the ammonium sulfate brine to 7.0 to 9.0 by addition of an alkaline material selected from the group consisting of alkali metal hydroxides, alkali metal carbonates, and ammonia;
   k. extracting the ammonium sulfate brine with cyclohexanone employing substantially all of cyclohexanone fed to the process, said extraction being carried out at a temperature of 70° to 95° C., whereby the hydrolyzed hydroxylamine monosulfonate is extracted and reacted with the cyclohexanone; and
   l. introducing the cyclohexanone extract into step (b).

2. The process of claim 1 wherein the reaction mixture in the first reaction zone is circulated at a rate of 20 to 60 times the rate of feed to such zone.

3. The process of claim 2 wherein the reaction is carried out in four zones.

4. The process of claim 3 wherein the reaction is at least 99 percent complete in the first reaction zone.

5. The process of claim 4 wherein the circulating reaction mixture in the first reaction zone has a pH of 7.0 to 7.5 and a temperature of 75° to 85° C.

6. The process of claim 5 wherein the extraction of the ammonium sulfate brine is carried out at a temperature of 75° to 85° C.

7. A continuous process for producing cyclohexanone oxime from cyclohexanone in two or more reaction zones, by action thereon of hydroxylamine in the form of a hydroxylamine reactant prepared by mixing ammonium hydroxylamine disulfonate with water and heating the resultant mixture to a temperature of 125° to 160° C. until at least 99.8% of the ammonium hydroxylamine monosulfonate produced in the hydrolysis is hydrolyzed, which process comprises:
   a. feeding substantially all of the hydroxylamine reactant to only the first reaction zone;
   b. adding cyclohexanone to the reaction mixture in the first reaction zone, said cyclohexanone being in the form of cyclohexanone extract containing hydroxylamine values recovered in step (k) of the process, said cyclohexanone being added to said first reaction zone with vigorous agitation of sufficient intensity to destroy localized concentrations of cyclohexanone in the reaction mixture;
   c. adding ammonia to the reaction mixture in the first reaction zone until the reaction mixture has a pH within the range of from 7.0 to 7.5;
   d. circulating the reaction mixture in the first reaction zone at a rate of 20 to 60 times the rate of feed of cyclohexanone to said zone;
   e. carrying out the reaction in the first reaction zone at a temperature of from 75° to 85° C., and establishing a circulating reaction mixture in the first reaction zone having a pH of 7.0 to 7.5 and a mol ratio of hydroxylamine:cyclohexanone of from 1.05:1 to 1.15:1;
   f. adding to the second and each subsequent zone, if any, a portion of the reaction mixture from the preceding zone;
   g. carrying out the reaction in the second and each subsequent reaction zone, if any, at a temperature of from 75° to 85° C. with agitation until conversion of the cyclohexanone to cyclohexanone oxime is substantially complete;
   h. withdrawing a stream comprising molten cyclohexanone oxime and ammonium sulfate brine from the last reaction zone;
   i. separating the molten cyclohexanone oxime from the ammonium sulfate brine;
   j. adjusting the pH of the ammonium sulfate brine to 7.5 to 9.0 by addition of ammonia;
   k. extracting the ammonium sulfate brine with cyclohexanone employing substantially all of cyclohexanone fed to the process, said extraction being carried out at a temperature of 75° to 85° C., whereby the hydrolyzed hydroxylamine monosulfonate is extracted and reacted with the cyclohexanone; and
l. introducing the cyclohexanone extract into step (b).

8. The process of claim 7 wherein the reaction mixture in the first reaction zone is circulated at a rate of about 40 times the rate of feed to such zone.

9. The process of claim 7 wherein the reaction is at least 99 percent complete in the first reaction zone, and the reaction is carried out in four zones.

10. The process of claim 7 wherein in step (j) the ammonium sulfate brine is adjusted to pH 7.5 to 8.5.

* * * * *